United States Patent [19]

Gianopoulos et al.

[11] Patent Number: 4,702,237
[45] Date of Patent: Oct. 27, 1987

[54] HEMORRHOID RETAINERS

[76] Inventors: Thomas J. Gianopoulos, 8070 12th Ave. South, Bloomington, Minn. 55420; Wallace W. Becklin, 10510 Holly La., Maple Grove, Minn. 55369

[21] Appl. No.: 902,068

[22] Filed: Aug. 27, 1986

Related U.S. Application Data

[63] Continuation of Ser. No. 690,619, Jan. 11, 1985, abandoned, which is a continuation-in-part of Ser. No. 393,132, Oct. 28, 1983.

[51] Int. Cl.⁴ ............................................. A61F 13/00
[52] U.S. Cl. .................... 128/98.1; 128/155; 128/168
[58] Field of Search .............. 128/98, 155, 156, 168, 128/169, 171; 604/337, 355

[56] References Cited

U.S. PATENT DOCUMENTS

| | | | |
|---|---|---|---|
| 96,460 | 11/1869 | Mervine, Jr. | 128/98 |
| 2,128,670 | 8/1938 | Bolder | 128/96 |
| 2,559,762 | 7/1951 | Furr | 128/98 |
| 2,615,445 | 10/1952 | Holmes | 128/98 |
| 2,653,599 | 9/1953 | Bell | 128/98 |
| 2,672,862 | 3/1954 | Krauss | 128/98 |
| 2,734,503 | 2/1956 | Doyle | 128/156 |
| 3,367,329 | 2/1968 | Dibelius | 128/156 |
| 3,529,597 | 9/1970 | Fuzak | 128/171 |
| 4,112,177 | 9/1978 | Salditt et al. | 128/156 X |

FOREIGN PATENT DOCUMENTS 0723431  2/1955  United Kingdom ................ 128/156

Primary Examiner—Robert A. Hafer
Assistant Examiner—Kathleen J. D'Arrigo
Attorney, Agent, or Firm—Jacobson and Johnson

[57] ABSTRACT

A flexible yet strong member having an adhesive on one side which can be secured to the anal area to physically hold the hemorrhoids within the anal orifice with the member including means such as orifices to permit bowel gas or flatulence to rapidly escape therethrough without dislodging the hemorrhoid retainer from the anal area.

8 Claims, 4 Drawing Figures

HEMORRHOID RETAINERS

CROSS REFERENCE TO RELATED APPLICATION

This application is a continuation of application Ser. No. 690,619, filed Jan. 11, 1985, now abandoned, which is a continuation-in-part of our U.S. patent application titled "HEM-AIDE MARK I", Ser. No. 393,132, deposited June 28, 1982, and filing completed on Oct. 28, 1983.

FIELD OF THE INVENTION

This invention relates primarily to medical devices and, more specifically, to disposable hemorrhoid retainers that can be quickly applied to securely and firmly hold hemorrhoids within the anal orifice.

BACKGROUND OF THE INVENTION

External protruding hemorrhoids generally cause pain and discomfort. In addition, if the hemorrhoids become bruised, they may bleed which may cause the person alarm and concern. Bleeding hemorrhoids may eventually require surgery since the available ointments, creams, jells and the like offer only temporary relief to the pain and itching and do not protect the hemorrhoid membranes from further bruising and bleeding. Typically, when external protruding hemorrhoids become bothersome, one must push the hemorrhoids into the anal area with one's fingers. However, insertion of the hemorrhoids into the anal area does not prevent the hemorrhoids from coming out again particularly if the person moves about. If the hemorrhoids continually protrude, usually the only option is to have surgery to remove them.

A disadvantage of available hemorrhoid preparations is that many people are hesitant about using them because they are, to some extent, invasive since some of the hemorrhoid preparations have to be placed inside the anal orifice.

The purpose of the present invention is to hold or retain hemorrhoids inside the anal orifice. If the hemorrhoids are held inside the anal orifice there is less chance of injury to the hemorrhoid membrane.

An advantage of our invention is that if the hemorrhoids are held within the anal orifice the bleeding is lessened and eventually may stop if our hemorrhoid retainer is used correctly and regularly. Therefore, it is an object of the present invention to fasten a hemorrhoid retainer around the anal area by means of an adhesive so as to firmly hold the hemorrhoids inside the anal orifice.

It is a further object of the present invention to prevent hemorrhoids from popping out at inopportune times.

It is an object of the present invention to make it unnecessary to continually have to push the hemorrhoids into the anal orifice such as with products such as jells, ointments, creams and the like.

It is an object of the present invention to possibly avoid hemorrhoidal surgery through regular and continual use of our retainer which holds the hemorrhoids inside the anal orifice.

It is an object of the present invention to allow flatulence to escape through the retainer to thereby eliminate dislodgement of the hemorrhoid retainer once it is installed.

It is an object of the present invention that as a consequence of using our invention over a period of time, it may not be necessary to continue to use our invention as the use of the invention may have a healing effect by preventing the hemorrhoids from being exposed to injury.

DESCRIPTION OF THE PRIOR ART

Other than surgery, the primary types of relief from pain of external hemorrhoids is the use of ointments, jells and creams which, by their own claims, give only temporary relief from hemorrhoidal pain. The hemorrhoid preparations presently on the market are intended as temporary relief agents. In addition, the available hemorrhoid preparations are messy and also soil the persons undergarments. Furthermore, none of these creams, ointments or jells truly solve the problem of keeping the hemorrhoids inside the anal orifice. That is, exertion or improper functioning of the anal sphincter may force the hemorrhoids out. The present invention, in contrast to the prior art jells and creams, supports and holds the hemorrhoids inside the anal orifice for prolonged periods of time.

There are known breathable tapes and bandaids which have been employed for other purposes. However, such devices are not suitable for use as a hemorrhoid retainer since they do not permit rapid escape of air therethrough. For example, Stenwell U.S. Pat. No. 3,888,247 shows a first aid bandage comprised of a microporous breathable surgical tape and a flexible backing. The Stenwell bandage is applied directly to the wound to maintain a proper positioning of the wound edges without interfering with the ventilation and drainage of the wound. This type of bandage is generally for wounds that require slow migration of air through the bandage, is unsuitable for use in anal areas since the flatulence would dislodge the bandage.

The Busee U.S. Pat. No. 3,763,858 shows a composite material with an adhesive for fastening two different materials together to form a breathable bandaid.

The Hodgson U.S. Pat. No. 3,645,835 shows a moisture-vapor-permeable pressure-sensitive adhesive material for use on animal skin and nails. However, no suggestion is made for use as a hemorrhoid retainer.

The Goldman U.S. Pat. No. 3,654,060 shows a multiply film or breathable sheeting which can be used as a protective covering in drapes or clothing for medical personnel and for hospitals.

SUMMARY OF THE INVENTION

The present invention comprises a flexible yet strong member having an adhesive on one side which can be secured to the anal area to physically hold the hemorrhoids within the anal orifice. The member includes means such as orifices to permit bowel gas or flatulence to rapidly escape therethrough without dislodging the hemorrhoid retainer.

DESCRIPTION OF THE PREFERRED EMBODIMENT

Figure 1:
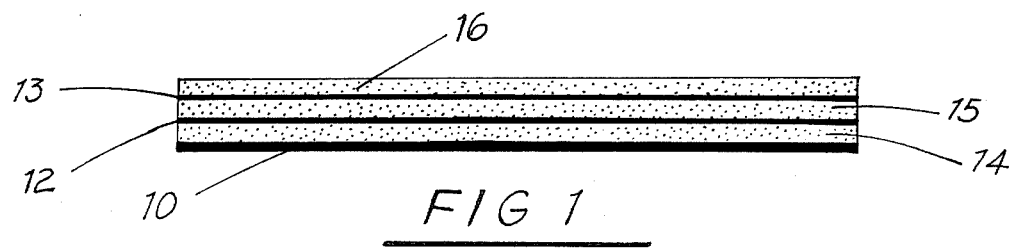
FIG. 1 is a front elevation of one embodiment of the present invention.
Figure 2:
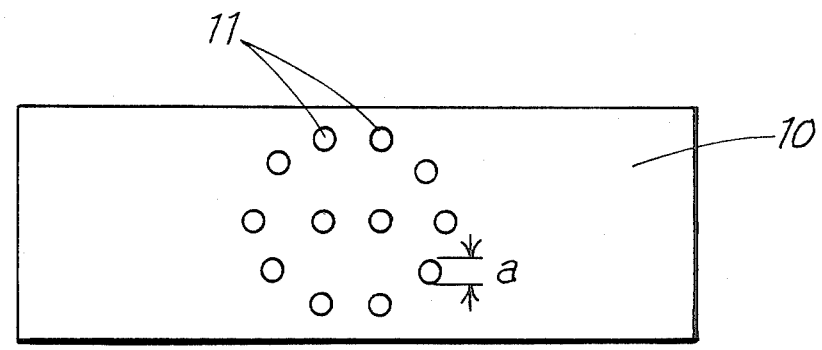
FIG. 2 is a top plan view of the invention shown in FIG. 1.

Referring to FIG. 1 and FIG. 2, reference numeral 10 identifies a multiple layered hemorrhoid retainer which comprises an oblong rectangular strip of non-toxic pure latex rubber 10. Located on one side of rubber 10 is a double-faced non-toxic tape 12 having an adhesive 14 on one side and an adhesive 15 on the opposite side. Adjacent to adhesive 15 is a single face non-toxic tape 13 which is located on adhesive 15 with its adhesive 16 exposed for application of retainer 10 to the anal area. Located in a spaced pattern that generally conforms to the shape of the anal opening is a plurality of openings 11 that extend completely through retainer 10. The holes or openings 11 have sufficiently open areas so as to allow rapid escape of flatulence therethrough without dislodging the retainer from the anal area.

In the application of our hemorrhoid retainer to the anal area one first pushes any external protruding hemorrhoids inside the anal orifice to permit the sphincter muscle to securely close. In order to obtain proper adhesion of the hemorrhoidal retainer, one should also clean and dry the anal area. Next, the hemorrhoidal retainer is applied to the anal area by positioning the retainer so that the openings 11 are located proximate the anal orifice. After proper positioning the hemorrhoid retainer one rubs the back of the hemorrhoid retainer 10 to force retainer 10 into adhesive contact with the anal area.

In the embodiment of FIG. 1 and FIG. 2 we preferably use a strip of non-toxic latex rubber 10 in conjunction with adhesive strips that can be used on humans. The use of latex rubber as the backing is preferable since it has sufficient strength to hold the hemorrhoids inside the anal orifice yet is sufficiently elastic enough to flex as the user moves about. In addition, the latex rubber does not irritate the user's skin and is therefore comfortable to wear for prolonged periods of time.

Figure 4:
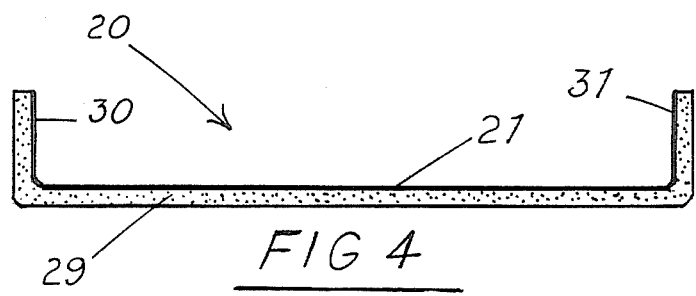
FIG. 4 is a side elevation view of the invention of FIG. 3 in an applied position.
Figure 3:
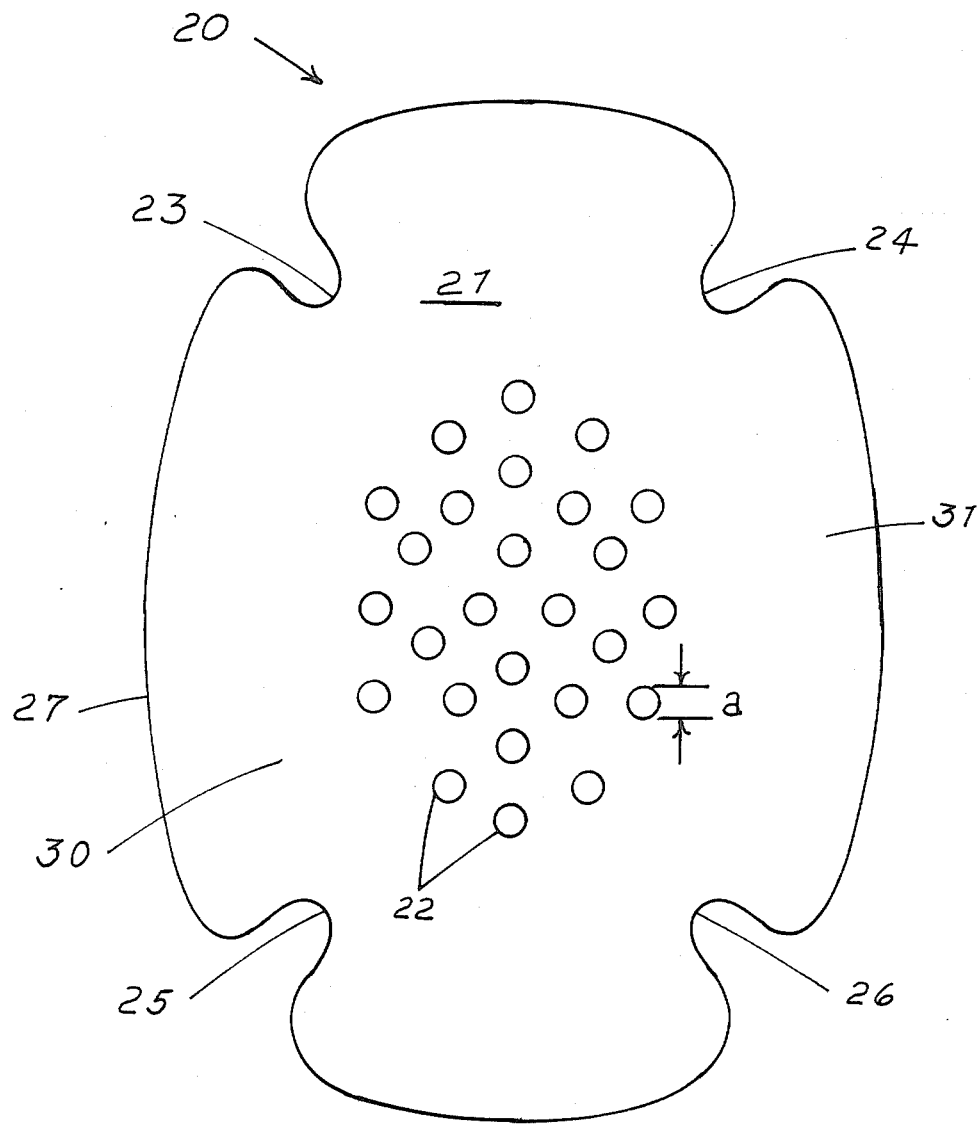
FIG. 3 is a top plan view of a second embodiment of the invention.

Referring to FIG. 3 there is shown our preferred embodiment comprising an oval shaped hemorrhoid retainer 20 including a single layer of material 21 which has sufficient strength to hold the hemorrhoids within the anal orifice yet sufficiently elastic so as to flex with movement of the user. Reference numeral 27 denotes the outer edge of retainer 20. Located in the central portion of hemorrhoid retainer 20 are a plurality of holes 22 having diameter a. The holes or vents 22 have sufficient open area so as to allow flatulence to rapidly escape therethrough. Located on the sides of retainer 20 are a plurality of relief areas. A first relief area 23, a second relief area 24, a third relief area 25 and a fourth relief area 26. Relief areas 24-26 coact to produce cutaway portions that permit side tab 31 to be folded as shown in FIG. 4. The purpose of the relief areas is to permit the hemorrhoid retainer to be fastened to both the anal area and the cheek area to thereby provide greater adhesion. The relief areas permit the side tabs of the hemorrhoid retainer to be folded over without producing creases or folds which would irritate the user. Consequently, our hemorrhoid retainer will securely and firmly hold the hemorrhoids in place yet be sufficiently comfortable so as not to annoy the user.

Typically the adhesives used to fasten our hemorrhoid retainer may be any adhesive which is non-toxic and which will adhere to the body. In use of the multiple layer embodiment in FIG. 1, we have found double-faced tape manufactured by the 3M medical group which can be applied to the non-toxic pure latex strip so that one side adheres to the latex. Next, a single-faced tape which is non-toxic and adheres to humans is applied to the opposite face. Typically a suitable single-faced adhesive tape is made by the Colgate-Palmolive Company for use on the human body and is sold under the name CUREX (trademark).

Although the embodiment of FIG. 1 shows two tapes in humans, the embodiment of FIG. 2 shows an example of a device which only one layer of support material is used and a single layer of adhesive is applied thereto.

We claim:

1. A hemorrhoid support device for a user having hemorrhoids that extend outside the anal orifice comprising a sheet having an adhesive layer on one side for attachment of said sheet to the anal area of the user having hemorrhoids that extend outside the anal orifice, said adhesive extending entirely across said sheet to thereby provide hemorrhoid support;

said sheet having sufficient flexibility so as to conform to the user's body movement yet sufficient strength so as to hold hemorrhoids within the anal orifice when said sheet is fastened over the anal orifice;

said sheet including at least one aperture to permit rapid egress of flatulence to thereby prevent flatulence from dislodging said hemorrhoid support device.

2. The invention of claim 1 wherein said hemorrhoid support device is generally oval shaped.

3. The invention of claim 1 wherein said invention includes relief areas to permit folding attachment of said invention to the anal area of a user.

4. The invention of claim 3 wherein said invention includes a plurality of tabs extending therefrom.

5. The invention of claim 1 wherein said sheet is latex rubber.

6. The method of preventing hemorrhoids from extending out of the anal orifice when the user moves about comprising the steps of:

pushing any external protruding hemorroids into the anal orifice;

cleaning the anal area to permit attachment of an adhesive-backed support sheet having at least one aperture positioned to permit rapid egress of flatulence thereto;

placing the adhesive-backed support sheet over the anal orifice to thereby adhesively contact the entire area around the anal orifice to provide a support to prevent hemorrhoids from popping out of the user's anal orifice as the user moves about.

7. The method of claim 6 wherein the adhesive backed support sheet has a plurality of openings and the step includes centering of the plurality of openings in the adhesive-backed support sheet over the anal orifice of the user.

8. The method of claim 7 wherein the user applies the hemorrhoid support device to the user's anal area.

* * * * *